US00PP24897P3

(12) United States Plant Patent
Korlipara

(10) Patent No.: US PP24,897 P3
(45) Date of Patent: Sep. 16, 2014

(54) ***ECHINACEA* PLANT NAMED 'CANTALOUPE'**

(50) Latin Name: ***Echinacea* hybrid**
Varietal Denomination: Cantaloupe

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 169 days.

(21) Appl. No.: 13/573,979

(22) Filed: Oct. 16, 2012

(65) Prior Publication Data

US 2014/0109277 P1 Apr. 17, 2014

(51) Int. Cl.
*A01H 5/00* (2006.01)

(52) U.S. Cl.
USPC ..... Plt./428

(58) Field of Classification Search
CPC ..... A01H 5/025; A01H 5/00; A01H 5/02
USPC ..... Plt./428
See application file for complete search history.

(56) References Cited

PUBLICATIONS

Upov Pluto Plant Variety Database 20140502, retrieved on May 22, 2014, retrieved from the Internet at <http://www.upov.int/pluto/en/index.jsp> for *Echinacea* 'Supreme Cantaloupe', one page.*

* cited by examiner

*Primary Examiner* — June Hwu
(74) *Attorney, Agent, or Firm* — Klarquist Sparkman, LLP

(57) ABSTRACT

A new and distinct *Echinacea* plant named 'Cantaloupe' characterized by enlarged disc florets forming an anemone-type inflorescence, cantaloupe orange ray and disc florets, inflorescences with dark centers when the disc florets are not fully opened, a medium short size and narrow, upright habit with excellent basal stem count and branching, and excellent vigor.

1 Drawing Sheet

Botanical denomination: *Echinacea* hybrid.
Variety designation: 'Cantaloupe'.

BACKGROUND OF THE INVENTION

The present invention relates to a new and distinct cultivar of *Echinacea* and given the cultivar name 'Cantaloupe'. *Echinacea* is in the family Asteraceae. The new cultivar is part of a planned breeding program for a series with compact habits and double "anemone"-type inflorescences. The exact parents of this selection are unknown, unnamed, proprietary interspecific hybrids of *Echinacea paradoxa*×*Echinacea purpurea*.

Compared to *Echinacea* 'Secret Desire' (U.S. Plant patent application Ser. No. 13/066,145, now U.S. Plant Pat. No. 23,085), the new cultivar is much shorter and has clear cantaloupe orange inflorescences rather than two-toned pink and soft orange.

Compared to *Echinacea* 'Marmalade' (U.S. Plant Pat. No. 22,602) the new cultivar has inflorescences a different shade of orange, cantaloupe orange rather than yellow orange.

This new *Echinacea* cultivar is distinguished by:

1. enlarged disc florets forming an anemone-type inflorescence,
2. cantaloupe orange ray and disc florets,
3. inflorescences with dark centers when the disc florets are not fully opened,
4. a medium short size and narrow, upright habit with excellent basal stem count and branching, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old plant of *Echinacea* 'Cantaloupe' growing in the trial bed in full sun in early July in Canby, Oreg.

DETAILED PLANT DESCRIPTION

The following is a detailed description of the new *Echinacea* cultivar based on observations of two-year-old specimens growing in the garden in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on *The Royal Horticultural Society Colour Chart,* $5^{th}$ edition.

Plant:

*Type*.—Herbaceous perennial.

*Hardiness*.—USDA Zones 4 to 9.

*Size*.—Grows to about 32 cm wide and 50 cm tall to top of inflorescences.

*Form*.—Basal clump, with about 14 stems from the base.

*Vigor*.—Excellent.

*Roots*.—Fibrous, with many downward growing and few laterals, ivory in color, Yellow White 158D, roots develop easily from cuttings from the crown Stem (flowering):

*Type*.—Ascending, with 1 to 8 inflorescences per stem.

*Size*.—To 45 cm tall to a terminal inflorescence and 8 mm wide at base.

*Internode length*.—2 cm to 4 cm.

*Surface texture*.—Strigose.

*Color*.—Yellow Green N144A.

Leaf (basal):

*Type*.—Simple.

*Shape*.—Ovate to lanceolate.

*Arrangement*.—Basal.

*Blade size*.—Grows to 10.5 cm long and 5.3 cm wide.

*Margins*.—Sparsely serrate.

*Apex*.—Acute.

*Base*.—Attenuate.

*Surface texture*.—Strigose on both sides.

*Venation*.—Pinnate, with 3 main veins from the base, Yellow Green 145D on top and bottom side.

*Color*.—Topside Green 137A, bottom side closest to Yellow Green 147B.

*Petiole description*.—Grows to 13 cm long and 3 mm wide above the clasp, sparsely strigose, Yellow Green 146C on sides, tinted Greyed Purple 187A at the base.

Leaf (stem):

*Type*.—Simple.

*Shape*.—Lanceolate.

*Arrangement*.—Alternate.

*Blade size*.—Grows to 12 cm long and 4 cm wide.

*Margins*.—Sparsely serrate.

*Apex*.—Acuminate.

*Base*.—Attenuate.

*Surface texture*.—Strigose on both sides.

*Venation*.—Pinnate, with 3 main veins from the base, Yellow Green 145D on top and bottom side.

*Color*.—Topside Green 137A, bottom side closest to Yellow Green 147B.

*Petiole description*.—On all but upper leaves, clasping, grows to 7.5 cm long and 2 mm wide above the clasp, strigose, both sides Yellow Green 146C on sides and 144D in center.

Inflorescence:

*Type*.—Composite on terminal stalked heads.

*Number of flowering stems per plant*.—About 35.

*Flowering stem*.—Grows to 45 cm tall from the base of the plant to the terminal inflorescence and can grow to 18 cm long from the top stem leaf to the base of an inflorescence; branched with 1 to 8 inflorescences per stem; diameter growing to 7 mm wide near the inflorescence; strigose; Yellow Green N144A.

*Size*.—Grows to 9 cm wide and 7 cm deep as disc enlarges.

*Form*.—Ray florets held slightly reflexed, mature disc is conic.

*Immature inflorescence*.—Grows to 3 cm wide and 2 cm deep, ray florets held at a 40 degree angle from the horizontal and rolled up so only the back color shows, Yellow Orange 18B, disc color Yellow Green 144A.

*Ray florets*.—Without pistil or stamen, about 21 to 37 in number, grow to 42 mm long and 9.5 mm wide, oblanceolate with the tip two-toothed, tips acute, entire margins, base attenuate, glabrous on both sides; top side between Orange 26A when first fully open changing to closest to Orange 26B on the top half blending to Orange Red 31C at the base, bottom side Orange Red 35D.

*Disc*.—Flat becoming conic, growing to 40 mm deep and 45 mm wide with maturity, Orange Red N34A when disc florets are closed to Orange 29A when disc florets are open.

*Disc florets*.—To about 400 in number, each with 1 pistil and 4 stamen, grow to 20 mm long and 5.5 mm wide, each with one persistent, very stiff linear bract (12 mm long with 2 mm Orange Red N34A at apex blending to 3 mm N34B to 4 mm Yellow Green 145D to White 155A at base); corollas to 17 mm long and 5.5 mm wide, tubular at base (2 mm to 3 mm long and 1.5 mm wide, 175A) then oblanceolate with tip 2 to 3 lobed (lobes lanceolate, to 4 mm long and 2 mm wide), margin entire, tips acute, base attenuate, glabrous on both sides, topside Orange 26A blending to Orange Red 31C at the base, bottom side Orange Red 37C; pistil 7 mm long, ovary 4.5 mm long, White NN155A, style 4 mm long Orange Red N34C, 2-branched stigma spreading, Orange Red N34C; stamen 4 mm long, filaments 3.5 mm long, threadlike, Orange Red 35D, anthers 2 mm long, Greyed Purple N186A, little pollen, Yellow Orange 22C.

*Phyllaries*.—In 4 leafy series, area grows to 32 mm wide and 10 mm deep, lobes lanceolate in shape, reflexed, grow to 17 mm long and 3 mm wide, both sides Yellow Green 147B, margins strigose, tip acute, strigose.

*Receptacle*.—Grows to 13 mm wide and 18 mm deep, White NN155B.

*Bloom period*.—July through October in Canby, Oreg.

*Fragrance*.—Sweet, floral.

*Lastingness*.—Each inflorescence lasts about two weeks in Canby, Oreg.

*Seeds*.—None seen.

*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

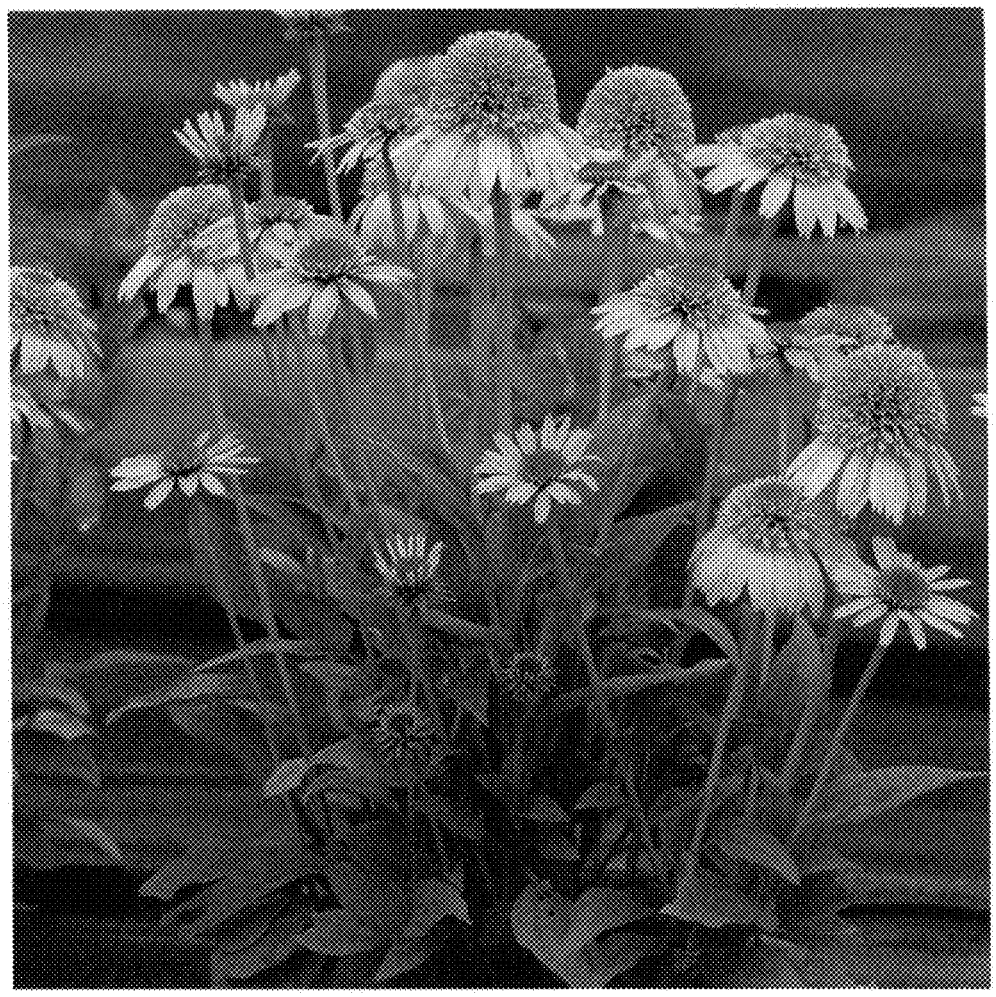

* * * * *